US006203981B1

United States Patent
Ackley et al.

(10) Patent No.: US 6,203,981 B1
(45) Date of Patent: Mar. 20, 2001

(54) TRANSISTOR-BASED MOLECULAR DETECTION APPARATUS AND METHOD

(75) Inventors: Donald Ackley, Cardiff, CA (US); Chan-Long Shieh, Paradise Valley; Thomas B. Harvey, III, Scottsdale, both of AZ (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/068,172

(22) PCT Filed: Apr. 4, 1997

(86) PCT No.: PCT/US97/05660

§ 371 Date: Feb. 8, 1999

§ 102(e) Date: Feb. 8, 1999

(87) PCT Pub. No.: WO97/39145

PCT Pub. Date: Oct. 23, 1997

Related U.S. Application Data

(63) Continuation of application No. 08/634,102, filed on Apr. 17, 1996, now abandoned.

(51) Int. Cl.[7] ........................................................ C12Q 1/68
(52) U.S. Cl. ................................ 435/6; 422/50; 422/68.1; 435/7.1; 435/7.2
(58) Field of Search .................................... 435/6, 7.1, 7.2; 422/50, 68.1

(56) References Cited

U.S. PATENT DOCUMENTS

| | | | |
|---|---|---|---|
| 4,490,216 | 12/1984 | Mc Connell | 204/1 T |
| 5,071,733 | 12/1991 | Uekita et al. | 430/326 |
| 5,074,977 | 12/1991 | Cheung et al. | 204/153.1 |
| 5,126,022 | 6/1992 | Soane et al. | 204/180.1 |
| 5,328,847 | 7/1994 | Case et al. | 435/291 |
| 5,391,507 | 2/1995 | Kwasnick et al. | 437/41 |
| 5,466,348 | 11/1995 | Holm-Kennedy | 204/153.1 |
| 5,495,184 | 2/1996 | Des Rosiers et al. | 326/73 |
| 5,527,670 | 6/1996 | Stanley | 435/6 |
| 5,532,128 | 7/1996 | Eggers et al. | 435/16 |
| 5,556,752 | 9/1996 | Lockhart et al. | 435/6 |
| 5,571,568 | * 11/1996 | Ribi et al. | 427/487 |
| 5,653,939 | 8/1997 | Hollis et al. | 422/50 |
| 5,776,672 | * 7/1998 | Hashimoto et al. | 435/6 |
| 5,827,482 | 10/1998 | Shieh et al. | 422/82.06 |

OTHER PUBLICATIONS

Storey, In Electronics A Systems Approach, pp. 176–177, 1992.

* cited by examiner

*Primary Examiner*—Ardin H. Marschel
(74) *Attorney, Agent, or Firm*—James E. Gauger

(57) ABSTRACT

Adjacent first and second transistors are integrated with a substrate. Each of the first and second transistors has a gate electrode, a source electrode, a drain electrode and a semiconductive channel formed of an organic material, the semiconductive channel electrically coupling the source electrode with the drain electrode. The source electrode of the first transistor is electrically coupled to the source electrode of the second transistor. A molecular receptor is bound directly to a surface of the semiconductive channel of the first transistor. A non-zero offset voltage, which produces equal channel currents in the semiconductive channels of the first and second transistors after a molecule has bound with the molecular receptor without a like binding event proximate to the second transistor, is sensed between the gate electrodes of the first and second transistors.

4 Claims, 5 Drawing Sheets

TRANSISTOR-BASED MOLECULAR DETECTION APPARATUS AND METHOD

This application is a 371 filing of PCT/US97/05660, filed Apr. 4, 1997; which is a Continuation of U.S. application Ser. No. 08/634,102; filed Apr. 17, 1996; and now abandoned.

FIELD OF THE INVENTION

The present invention relates to molecular detection devices.

BACKGROUND OF THE INVENTION

Recently, an increased effort has been directed toward the development of chips for molecular detection. In general, a molecular detection chip includes a substrate on which an array of binding sites is arranged. Each binding site (or hybridization site) has a respective molecular receptor which binds or hybridizes with a molecule having a predetermined structure. A sample solution is applied to the molecular detection chip, and molecules in the sample bind or hybridize at one or more of the binding sites. The particular binding sites at which hybridization occurs are detected, and one or more molecular structures within the sample are subsequently deduced.

Of great interest are molecular detection chips for gene sequencing. These chips, often referred to as DNA chips, utilize an array of selective binding sites each having respective single-stranded DNA probes. A sample of single-stranded DNA fragments, referred to as target DNA, is applied to the DNA chip. The DNA fragments attach to one or more of the DNA probes by a hybridization process. By detecting which DNA probes have a DNA fragment hybridized thereto, a sequence of nucleotide bases within the DNA fragment can be determined.

To hasten the hybridization process, a local concentration of target DNA can be increased at predetermined sites using electric field enhancements. Here, each site has an electrode associated therewith for selectively generating an electric field thereby. The electric field is generated by applying an electric potential between an electrode at the site and a counter electrode at a peripheral portion of the chip. To attract DNA fragments to the site, the polarity of the electric potential is selected to generate an electric field having a polarity opposite to the charge of the DNA fragments. To de-hybridize the site, an electric field having the same polarity as the DNA fragments can be generated to repel the DNA fragments from the site.

Various approaches have been utilized to detect a hybridization event at a binding site. In one approach, a radioactive marker is attached to each of a plurality of molecules in the sample. The binding of a molecule to a molecular receptor is then detectable by detecting the radioactive marker.

Other approaches for detection utilize fluorescent labels, such as fluorophores which selectively illuminate when hybridization occurs. These fluorophores are illuminated by a pump light source external to the substrate. An external charge-coupled device (CCD) camera is utilized to detect fluorescence from the illuminated fluorophores.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

DETAILED DESCRIPTION OF A PREFERRED EMBODIMENT

Embodiments of the present invention advantageously provide a molecular detection apparatus which detects the binding or hybridization of a molecule to a molecular receptor by sensing a charge associated with the molecule. A preferred embodiment utilizes a thin-film transistor integrated with a substrate to define a binding site. The thin-film transistor is utilized both to detect binding events and to control hybridization and de-hybridization. The sensitivity of detection can be enhanced by forming a differential pair using the transistor and a second transistor at an unhybridized site.

Figure 1:
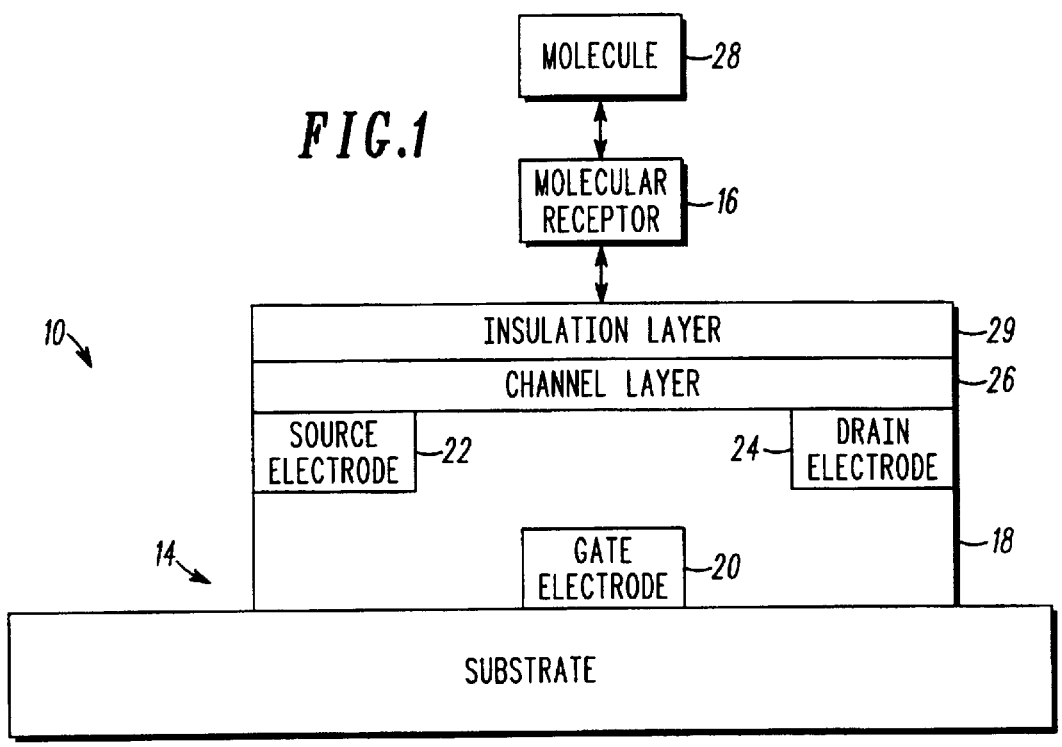
FIG. 1 is a block diagram of an embodiment of a molecular detection apparatus in accordance with the present invention.

FIG. 1 is a block diagram of an embodiment of a molecular detection apparatus 10 in accordance with the present invention. The molecular detection apparatus 10 includes a substrate 12 which supports a binding site 14 for receiving a molecular receptor 16. In general, the molecular receptor 16 is selected in dependence upon a type of molecule which is to be detected. The molecular receptor 16 typically includes a biological or synthetic molecule that has a specific affinity to the molecule to be detected. The molecular receptor 16 can include a chain of at least one nucleotide which hybridizes with a complementary chain of at least one nucleotide included in the molecule. Here, for example, the molecular receptor 16 can include a DNA probe for detecting a corresponding, complementary DNA sequence in the molecule. It is noted, however, that the scope of the invention is not limited to sensing the hybridization of DNA molecules. For example, embodiments of the present invention can be utilized to detect RNA hybridization and antibody-antigen binding events.

The molecular detection apparatus 10 further includes a transistor 18 integrated or fabricated in the substrate 12. The transistor 18 has a gate electrode 20, a source electrode 22, and a drain electrode 24. A semiconductive channel layer 26 in the transistor 18 electrically couples the source electrode 22 to the drain electrode 24. The semiconductive channel layer 26 is located proximate to the binding site 14 so that a conductance between the source electrode 22 and the drain electrode 24 is modified by a charge associated with a molecule 28 when the molecule 28 binds with the molecular receptor 16. The binding of the molecule 28 to the molecular receptor 16 is sensed by sensing a modified electrical characteristic of the transistor 18 which results from the charge associated with the molecule being proximate to the semiconductive channel layer 26.

The charge associated with the molecule 28 can be inherent in the molecule 28, such as the inherent charge in a DNA molecule. The charge associated with the molecule 28 may also result from a charged member attached to the molecule 28. For example, the charge associated with the molecule 28 can result from a charged bead being attached to the molecule 28.

Various known technologies can be utilized to form the transistor 18. In a preferred embodiment, the transistor 18 is a thin-film transistor (TFT). Using thin-film technology, the semiconductive channel layer 26 can be formed of an organic material which allows the molecular receptor 16 to be bound directly to a surface of the semiconductive channel layer 26. Alternatively, the semiconductive channel layer 26 can be formed of silicon (such as a-Si or poly-Si), in which case an insulation layer 29 can be disposed between the molecular receptor 16 and a surface of the semiconductive channel layer 26 to provide appropriate passivation. The insulation layer 29 can be in the form of a surface oxide layer.

To enhance the hybridization process, the apparatus can include an attachment layer on which the molecular receptor 16 is bound. The attachment layer is disposed between the molecular receptor 16 and the surface of either the semiconductive channel layer 26 or the insulation layer 29.

Figure 2:
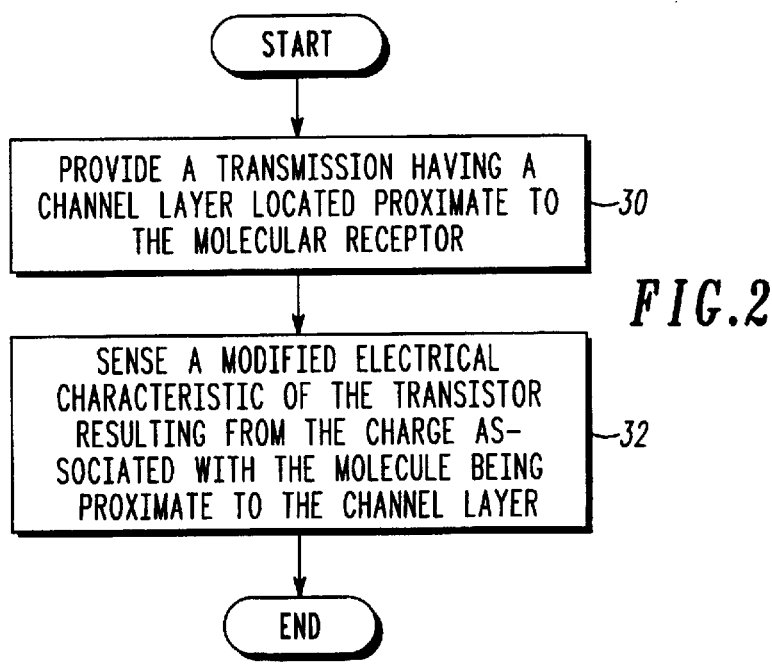
FIG. 2 is a flow chart of an embodiment of a method of sensing a binding of a molecule to a molecular receptor at a binding site in a molecular detection apparatus.

FIG. 2 is a flow chart of an embodiment of a method of sensing a binding of a molecule to a molecular receptor at a binding site in a molecular detection apparatus. As indicated by block 30, the method includes a step of providing a transistor having a semiconductive channel layer located proximate to the molecular receptor so that a conductance between a source electrode and a drain electrode is modified by a charge associated with the molecule when the molecule hybridizes with the molecular receptor. This step can be performed by utilizing an embodiment of a molecular detection apparatus as described herein.

As indicated by block 32, the method includes a step of sensing a modified electrical characteristic of the transistor which results from the charge associated with the molecule being proximate to the semiconductive channel layer upon binding. This step of sensing the modified electrical characteristic can be performed in a variety of ways, three of which being described below.

Figure 3:
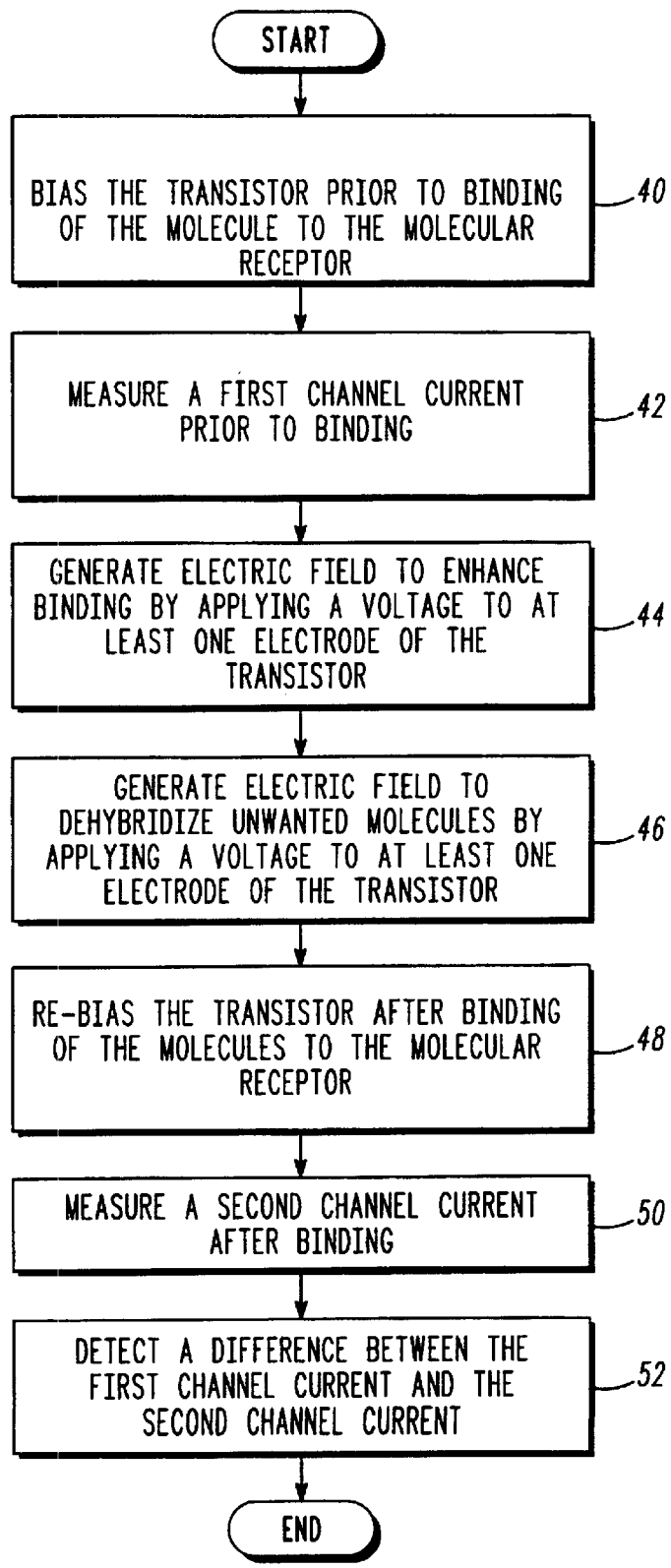
FIG. 3 is a flow chart of an embodiment of a method of sensing a modified electrical characteristic of the transistor.

FIG. 3 is a flow chart of an embodiment of a method of sensing a modified electrical characteristic of the transistor. As indicated by block 40, the method includes a step of biasing the transistor in a predetermined manner prior to the binding of the molecule with the molecular receptor. Here, a respective, predetermined voltage level is applied to each of the gate electrode, the drain electrode, and the source electrode of the transistor.

As indicated by block 42, a step of measuring a first channel current between the drain electrode and the source electrode is performed prior to the binding of the molecule with the molecular receptor. The first channel current results from the biasing of the transistor performed in the previous step.

After measuring the first channel current, the molecule is allowed to hybridize or bind with the molecular receptor. As indicated by block 44, the binding can be field-enhanced by performing a step of applying a first voltage to at least one of the gate electrode, the source electrode, and the drain electrode. The first voltage is selected to generate an electric field which attracts the molecule to the binding site.

After hybridization, an optional step of dehybridizing any unwanted molecules from the binding site can be performed. Specifically, as indicated by block 46, a step of dehybridization can be performed by applying a second voltage to at least one of the gate electrode, the source electrode, and the drain electrode. The second voltage is selected to provide an electric field which repels unwanted molecules from the binding site. The unwanted molecules can include partially-bound molecules, for example.

As indicated by block 48, a step of re-biasing the transistor is performed. Here, the transistor is biased in the same predetermined manner as in the step indicated by block 40.

As indicated by block 50, a step of measuring a second channel current between the drain electrode and the source electrode is performed after the binding of the molecule with the molecular receptor. The second channel current results from the biasing of the transistor performed in the previous step. Preferably, the first channel current and the second channel current are measured for a fixed voltage applied to the gate electrode.

The modified electrical characteristic is sensed by a step of detecting a difference between the first channel current and the second channel current, indicated by block 52. For example, the modified electrical characteristic may be determined when a difference between the first channel current and the second channel current is beyond a predetermined threshold.

Figure 4:
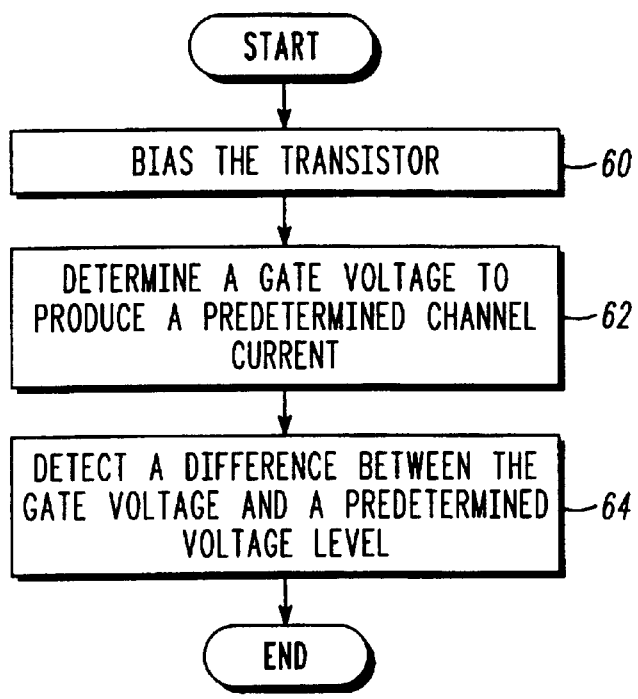
FIG. 4 is a flow chart of another embodiment of a method of sensing a modified electrical characteristic of the transistor.

FIG. 4 is a flow chart of another embodiment of a method of sensing a modified electrical characteristic of the transistor. As indicated by block 60, the method includes a step of biasing the transistor in a predetermined manner. Here, a respective, predetermined voltage level is applied to each of the drain electrode and the source electrode of the transistor.

As indicated by block 62, a step of determining a voltage for the gate electrode to produce a predetermined channel current is performed. In one embodiment, the predetermined channel current is selected to be near zero. Here, the voltage applied to the gate electrode is varied to determine a threshold voltage which nulls out the channel current. The threshold voltage which nulls the channel current is proportional to the amount of charge incorporated into the channel layer by the binding. It is noted that the predetermined channel current need not be near zero in alternative embodiments.

The modified electrical characteristic is sensed by a step, indicated by block 64, of detecting a difference between a predetermined voltage level and the voltage determined in the above-described step. The predetermined voltage level can be, for example, a voltage which produces the predetermined channel current before hybridization. Hence, the modified electrical characteristic may be determined when the gate voltage (post-hybridization) which produces the predetermined channel current is beyond a predetermined threshold.

Figure 5:
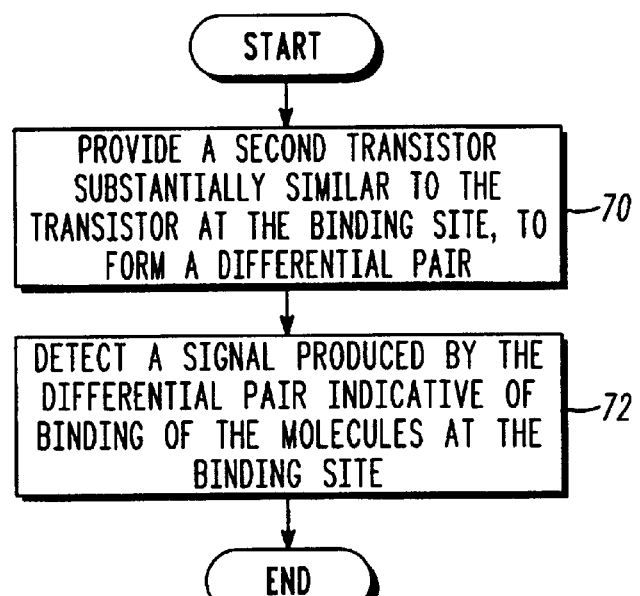
FIG. 5 is a flow chart of yet another embodiment of a method of sensing a modified electrical characteristic of the transistor.

FIG. 5 is a flow chart of yet another embodiment of a method of sensing a modified electrical characteristic of the transistor. As indicated by block 70, the method includes a step of providing a second transistor which is substantially similar to the transistor at the binding site. The second transistor, however, is located at an unhybridized site on the molecular detection apparatus. The second transistor is electrically connected with the transistor to form a differential pair. As indicated by block 71, a step of detecting a signal, produced by the differential pair, indicative of a binding of the molecule at the binding site is performed.

Figure 6:
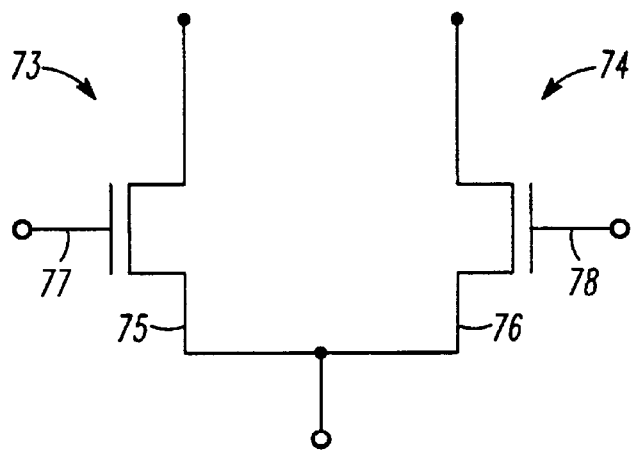
FIG. 6 schematically illustrates a differential pair formed by a first transistor and a second transistor.

FIG. 6 schematically illustrates a differential pair 72 formed by a first transistor 73 and a second transistor 74. The first transistor 73 is located at a binding site while the second transistor 74 is located at an unhybridized site. Physically, the first transistor 73 and the second transistor 74 can be located adjacent one another on a substrate. The differential pair is formed by coupling a source electrode 75 of the first transistor 73 to a source electrode 76 of the second transistor 74.

A binding event can be detected by applying a common voltage to gate electrodes 77 and 78, and detecting a difference in channel currents between the first transistor 73 and the second transistor 74. Alternatively, the binding event can be detected by detecting a non-zero offset voltage between the gate electrodes 77 and 78 which produces equal channel currents for the first transistor 73 and the second transistor 74.

Figure 7:
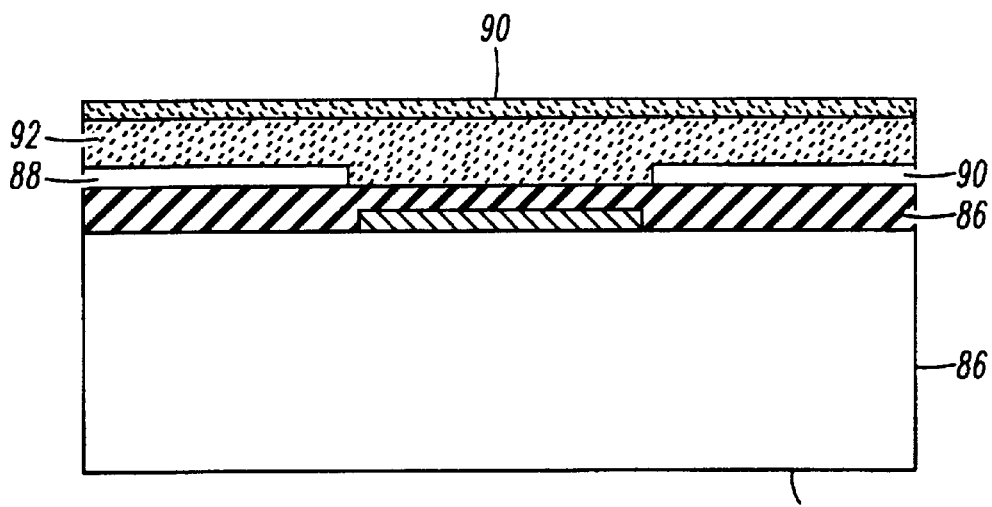
FIG. 7 is a cross-sectional view of another embodiment of an apparatus for sensing a binding of a molecule at a binding site in a molecular detection apparatus.

FIG. 7 is a cross-sectional view of another embodiment of an apparatus for sensing a binding of a molecule at a binding site in a molecular detection apparatus. This embodiment utilizes a thin-film transistor 80 formed on a substrate 82. Disposed on a top surface of the substrate 82 are a gate electrode 84 and an insulation layer 86. A source electrode 88, a drain electrode 90, and a channel layer 92 are formed on a top surface of the insulation layer 86.

A molecular receptor, such as a single-stranded DNA molecule 94, is located in proximity to the channel layer 92. As illustrated, the single-stranded DNA molecule 94 can be attached directly to a surface of the channel layer 92. As described earlier, the channel layer 92 can be formed of an organic material which allows the single-stranded DNA molecule 94 to be directly attached to the surface. Here, the organic material is selected to be compatible with the DNA species and to optimize the attachment of DNA fragments to the surface.

By burying the gate electrode 84, the source electrode 88, and the drain electrode 90 beneath the channel layer 92, difficulties associated with potential-induced denaturation at the electrodes are prevented.

Figure 8:
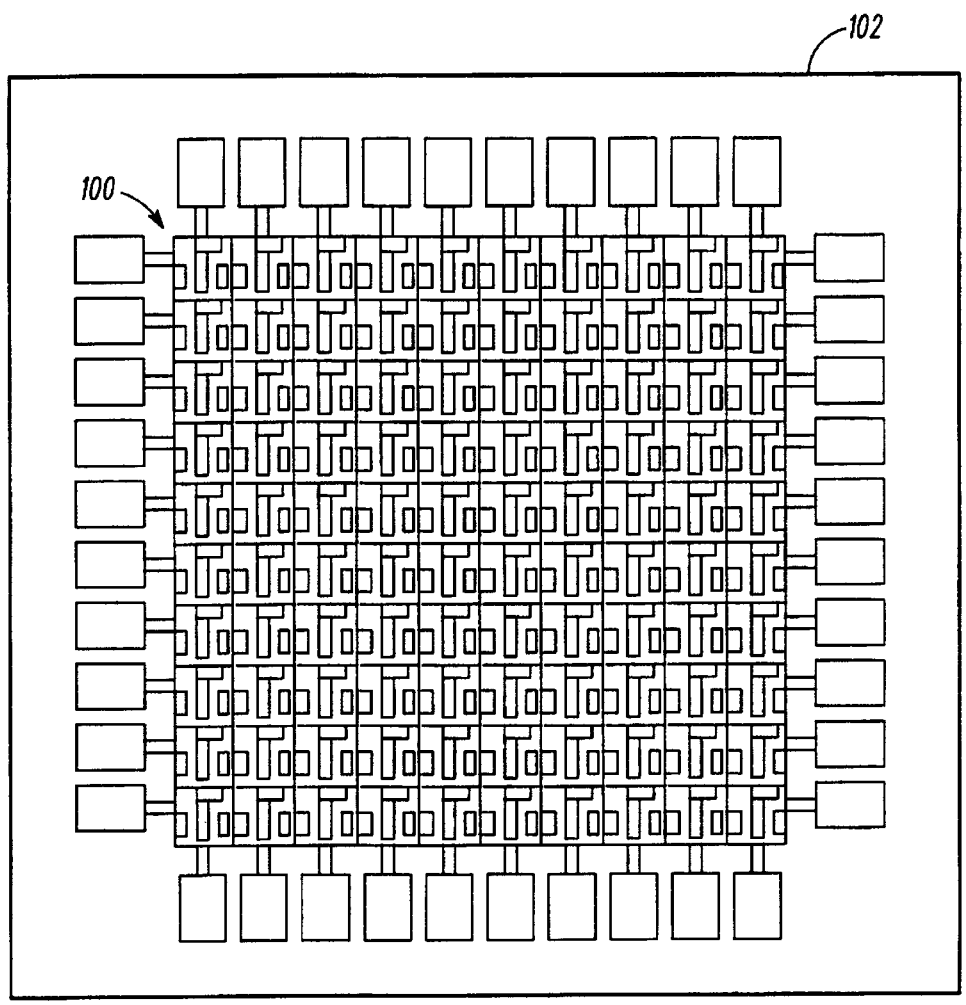
FIGS. 8 and 9 illustrate a top view and a side view, respectively, of an embodiment of an integrated molecular detection apparatus in accordance with the present invention.
Figure 9:
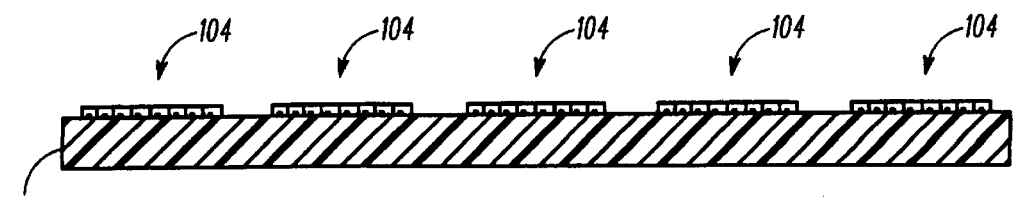

FIGS. 8 and 9 illustrate a top view and a side view, respectively, of an embodiment of an integrated molecular detection apparatus in accordance with the present invention. The integrated molecular detection apparatus includes an array of thin-film transistors 100 fabricated on a top surface of a substrate 102. The thin-film transistors 100 can be formed in a manner similar to that used to construct active matrix displays.

Each of the thin-film transistors 100 is located proximate to a respective one of plurality of binding sites 104. Specific DNA probes are deposited onto each of the thin-film transistors 100. The DNA probes can be deposited using conventional robotic dispensing techniques, or can be bound specifically into a channel of the thin-film transistors 100 using binding techniques known in the art.

In operation as a sequencer or a diagnostic tool, DNA sequences in a sample analyte hybridize onto selective ones of the binding sites 104. Field-assisted or thermally-assisted hybridization techniques can be utilized to enhance the hybridization process. After hybridization, unwanted sequences with only partial binding can be dehybridized using field enhancement by switching appropriate biases onto at least one electrode of the thin-film transistors 100. Alternatively, thermal desorption can be utilized to dehybridize unwanted sequences.

Thereafter, each of the thin-film transistors 100 is biased for transistor operation. As described earlier, a gate voltage for each of the thin-film transistors 100 can be varied to null out a respective channel current. The gate voltage required to null out the respective channel current is proportional to an amount of charge incorporated in the thin-film transistor. The value of the gate voltage can be read-out through the active matrix. As previously described, alternative approaches to detecting binding events include, but are not limited to, detecting a variation in channel current (measured before and after hybridization) for a fixed gate voltage, and detecting a signal produced by a differential pair of thin-film transistors.

Thus, there has been described herein a concept, as well as several embodiments including preferred embodiments of a transistor-based molecular detection apparatus and method.

Because the various embodiments of the present invention detect a binding event by sensing a charge associated with a target molecule, they provide a significant improvement in that a transistor integrated in the molecular detection apparatus can be utilized to electronically detect the target molecule. To improve detection, the charge associated with the target molecule can be enhanced by attaching a charged bead to the target molecule.

Additionally, the various embodiments of the present invention as herein-described utilize electrodes in the transistor to perform field-assisted hybridization and dehybridization.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A molecular detection method comprising the steps of:

providing a substrate;

providing a first transistor integrated with the substrate, the first transistor having a gate electrode, a source electrode, a drain electrode and a semiconductive channel which electrically couples the source electrode with the drain electrode, the semiconductive channel formed of an organic material;

providing a molecular receptor bound directly to a surface of the semiconductive channel of the first transistor;

providing a second transistor integrated with the substrate and adjacent the first transistor, the second transistor having a gate electrode, a source electrode, a drain electrode and a semiconductive channel which electrically couples the source electrode with the drain electrode, the semiconductive channel formed of an organic material, the source electrode electrically coupled to the source electrode of the first transistor; and sensing a non-zero offset voltage between the gate electrode of the first transistor and the gate electrode of the second transistor which produces equal channel currents in the semiconductive channels of the first transistor and the second transistor after a molecule has bound with the molecular receptor without a like binding event proximate to the second transistor.

2. The molecular detection method of claim 1 wherein the molecular receptor comprises a chain of a plurality of nucleotides.

3. The molecular detection method of claim 1 wherein the molecular receptor is receptive to a chain of a plurality of nucleotides.

4. The molecular detection method of claim 1 wherein the molecular receptor is receptive to a DNA molecule.

* * * * *